United States Patent
Wang et al.

(10) Patent No.: US 6,673,313 B2
(45) Date of Patent: Jan. 6, 2004

(54) STERILIZING A DEVICE BY REVAPORIZING A CONDENSED VAPOR

(75) Inventors: Jenn-Hann Wang, Mission Viejo, CA (US); Szu-Min Lin, Laguna Hills, CA (US); Paul T. Jacobs, Trabuco Canyon, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/187,128

(22) Filed: Jun. 28, 2002

(65) Prior Publication Data

US 2003/0017074 A1 Jan. 23, 2003

Related U.S. Application Data

(63) Continuation of application No. 09/223,594, filed on Dec. 30, 1998, now Pat. No. 6,451,254.

(51) Int. Cl.⁷ ................................................. A61L 2/20
(52) U.S. Cl. ........................................................ 422/33
(58) Field of Search ................................. 422/27, 33

(56) References Cited

U.S. PATENT DOCUMENTS

| | | | |
|---|---|---|---|
| 4,169,123 A | | 9/1979 | Moore et al. |
| 4,169,124 A | * | 9/1979 | Forstrom et al. ............. 422/33 |
| 4,207,286 A | | 6/1980 | Gut Boucher ............... 422/28 |
| 4,225,556 A | * | 9/1980 | Lothman et al. .............. 422/28 |
| 4,512,951 A | * | 4/1985 | Koubek ....................... 422/33 |
| 4,643,876 A | | 2/1987 | Jacobs et al. |
| 4,650,646 A | | 3/1987 | Cummings et al. |
| 4,797,255 A | * | 1/1989 | Hatanaka et al. ............. 422/28 |
| 4,898,715 A | | 2/1990 | Jacob .......................... 422/22 |
| 4,943,414 A | * | 7/1990 | Jacobs et al. .................. 422/28 |
| 4,952,370 A | * | 8/1990 | Cummings et al. ........... 422/28 |
| 5,087,418 A | | 2/1992 | Jacob .......................... 422/28 |
| 5,200,146 A | | 4/1993 | Goodman .................... 422/28 |
| 5,288,460 A | | 2/1994 | Caputo et al. ................ 422/28 |
| 5,492,672 A | | 2/1996 | Childers et al. |
| 6,068,817 A | | 5/2000 | Addy et al. ................... 422/33 |
| 6,451,255 B1 | | 9/2002 | Williams et al. .............. 422/33 |

* cited by examiner

*Primary Examiner*—Elizabeth McKane

(57) ABSTRACT

A method for sterilizing the interior of a diffusion restricted area by introducing a sterilant in a chamber, condensing the vapor, reducing the pressure in the chamber to revaporize the condensed vapor, and maintaining the device in the chamber until the device is sterilized. The sterilant has a vapor pressure less than the vapor pressure of water and is preferably hydrogen peroxide. The pressure in the chamber while maintaining the device in the chamber may be held constant, varied, or increased. Plasma may additionally be introduced into the chamber to improve the rate of sterilization.

29 Claims, 1 Drawing Sheet

STERILIZING A DEVICE BY REVAPORIZING A CONDENSED VAPOR

RELATED APPLICATION INFORMATION

This application is a continuation of U.S. application Ser. No. 09/223,594, filed Dec. 30, 1998, now U.S. Pat. No. 6,451,254, which is hereby incorporated by reference in its entirety.

FIELD OF THE INVENTION

This invention relates to a method of sterilizing a diffusion-restricted area in a chamber by condensing a vapor sterilant in the chamber, and revaporizing the condensed vapor sterilant.

BACKGROUND OF THE INVENTION

Medical instruments have traditionally been sterilized either by heat, especially steam, or with a chemical, such as formaldehyde or ethylene oxide. There are drawbacks to both of these sterilization methods.

Many medical devices are sensitive to heat, moisture, or both. Formaldehyde and ethylene oxide are both toxic gases that pose potential hazards to healthcare workers.

Sterilization with liquid hydrogen peroxide has been found to require high concentrations of sterilant, long exposure times and/or high temperatures. Sterilization with hydrogen peroxide vapor rather than liquid hydrogen peroxide has advantages over other chemical sterilization approaches (see, for example, U.S. Pat. Nos. 4,169,123 and 4,169,124). The combination of hydrogen peroxide with a plasma provides certain additional advantages, as disclosed in U.S. Pat. No. 4,643,876, issued to Jacobs et al.

While sterilization with hydrogen peroxide vapor in combination with a plasma has been found to be effective in sterilizing "open" systems, it is not effective in sterilizing articles having diffusion-restricted areas, because the method is dependent on diffusing the vapor sterilant into close proximity with the article to achieve sterilization. Articles having diffusion-restricted areas such as the interior of lumens, are sterilized only with high concentrations of sterilant, extended exposure times and/or elevated temperatures. Sterilization of long, narrow lumens therefore is a challenge.

Sterilization methods that use hydrogen peroxide vapor generated from an aqueous solution of hydrogen peroxide have certain disadvantages because:

1. Water has a higher vapor pressure than hydrogen peroxide and will vaporize faster than hydrogen peroxide from an aqueous solution.
2. Water has a lower molecular weight than hydrogen peroxide and will diffuse faster than hydrogen peroxide in the vapor state.

Because of these factors, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion restricted areas, such as small crevices and long, narrow lumens. One cannot solve the problem by using more concentrated hydrogen peroxide, because concentrated solutions of hydrogen peroxide at concentrations greater than 65% can be hazardous, because of the strong oxidizing nature.

Cummings et al. (U.S. Pat. No. 4,952,370) discloses a sterilization process where aqueous hydrogen peroxide vapor is first condensed on the article to be sterilized, and then a source of vacuum is applied to the sterilization chamber to remove the water and hydrogen peroxide from the article. The liquid peroxide on the article is effective at sterilizing the surface, but it is ineffective at sterilizing diffusion-restricted areas, such as the interior of lumens, because the method still depends on the diffusion of hydrogen peroxide vapor into the lumen to effect sterilization.

Jacobs et al. (U.S. Pat. No. 4,943,414) discloses a process in which a vessel containing a small amount of vaporizable liquid sterilant solution is attached to a lumen, and the sterilant vaporizes and flows directly into the lumen as the pressure is reduced during the sterilization cycle. This system has the advantage that the water and hydrogen peroxide vapor are pulled through the lumen by the vacuum, increasing the sterilization rate for lumens, but it has the disadvantage that a vessel must be attached to each lumen to be sterilized. Potentially, the area between the vessel and the lumen may be occluded from the sterilization process. In addition, water vaporizes more rapidly than the hydrogen peroxide, and it precedes the hydrogen peroxide vapor into the lumen.

Childers et al. (U.S. Pat. No. 5,492,672) discloses a process for sterilizing narrow lumens. The process uses a multicomponent vapor sterilant and requires successive alternating periods of flow of vapor sterilant and discontinuance of the flow. A complex apparatus is used to accomplish the method. Because flow through of vapor is used, closed end lumens are not readily sterilized by the method.

There is a need for a simple and effective method of sterilizing the interior of long, narrow lumens.

SUMMARY OF THE INVENTION

One aspect of the present invention relates to a method for enhancing the sterilization of a lumen device in a chamber. The method comprises introducing sterilant into the chamber from a source of sterilant, condensing the vapor sterilant in the chamber, reducing the pressure in the chamber below the vapor pressure of the vapor sterilant to revaporize the condensed vapor, and maintaining the device in chamber until it is sterilized.

Preferably, the sterilant comprises hydrogen peroxide. Advantageously, the sterilant has a vapor pressure less than the vapor pressure of water. The source of sterilant preferably comprises hydrogen peroxide. The source of sterilant can be a liquid, aqueous solution, or a solid. Advantageously, the source of sterilant is in an enclosure in fluid communication with the chamber. Preferably, the source of sterilant in the enclosure is a liquid, and the liquid is vaporized into the chamber. The source of sterilant can also be located in the chamber.

Advantageously, the source of sterilant is concentrated while it is introduced into the chamber. In some embodiments, the source of sterilant is a solid peroxide complex. Preferably, the vapor sterilant is condensed inside the lumen.

Condensing the vapor can comprise increasing the pressure in the chamber to above the vapor pressure of the vapor sterilant, venting the chamber to atmospheric pressure, introducing more sterilant into the chamber, or reducing the pressure in the chamber below the vapor pressure of the vapor sterilant and then increasing the pressure in the chamber to condense the vapor sterilant.

Advantageously, the pressure in the chamber is controlled by opening or closing a valve between the chamber and a vacuum pump. One or more steps of the method can be repeated one or more times in any order.

Preferably, at least a portion of the condensed vapor is inside the lumen, and the condensed vapor inside the lumen is revaporized. Advantageously, revaporizing the condensed vapor in the chamber also concentrates the vapor sterilant.

Maintaining the device in the chamber can comprise maintaining the chamber at constant pressure, varying the pressure in the chamber, reducing the pressure in the chamber, or increasing the pressure in the chamber. Advantageously, the device is also exposed to plasma. Preferably, the exterior of the device is sterilized prior to reducing the pressure in the chamber and revaporizing the condensed vapor. In some embodiments, the revaporizing is repeated.

DETAILED DESCRIPTION OF THE PREFERRED EMBODIMENT

Figure 1:
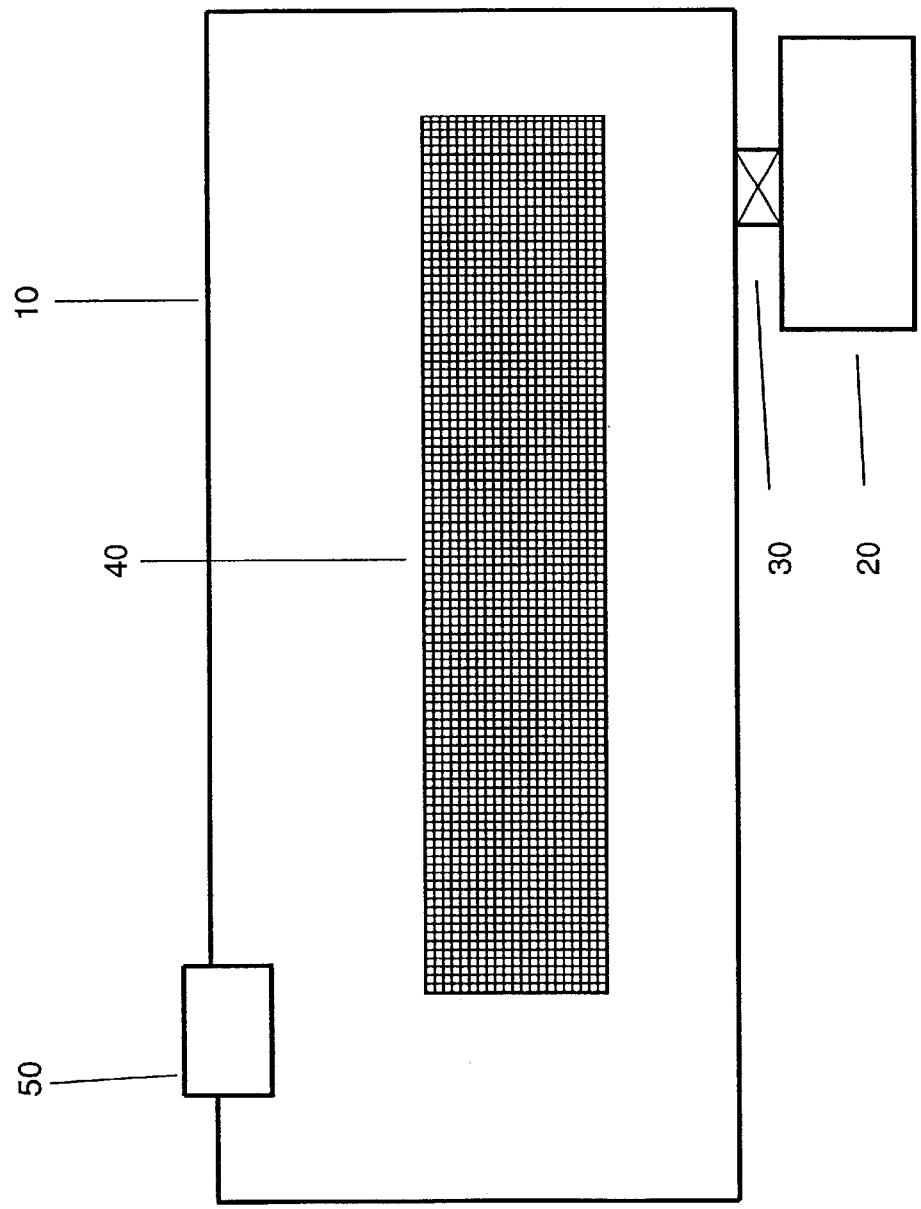
FIG. 1 is a drawing showing a sterilizer and vaporizer with a tray of equipment to be sterilized.

Sterilizing the interior of lumened devices poses a challenge to sterilization systems. Achieving rapid sterilization of lumened devices or other diffusion restricted articles at low temperatures with low concentrations of sterilant represents an even greater challenge.

In the present invention, the shortcomings of previous sterilization systems are overcome by introducing condensable vapor sterilant into the sterilizer, condensing the vapor sterilant in the sterilizer, lowering the pressure in the sterilizer to revaporize the condensed vapor, and maintaining the device in the sterilizer until the device is sterilized.

Although one preferred condensable vapor comprises peroxide, particularly hydrogen peroxide, other vapor sterilants can be used in the method. In order to be used in the method of the invention, the sterilant must have a lower vapor pressure than water. Hydrogen peroxide is preferred.

The source of hydrogen peroxide can be a liquid or a solid. In one embodiment, the solid source of hydrogen peroxide comprises a solid peroxide complex. The solid peroxide complex can be either an organic complex or an inorganic complex.

FIG. 1 shows one suitable form of apparatus for practicing the method of the present invention. The apparatus of FIG. 1 was used to generate the data in the Examples below. It should be understood that the method is not limited to the apparatus of FIG. 1 and that other suitable forms of apparatus for practicing the method of the present invention will be obvious to those of ordinary skill in the art.

A sterilization chamber 10 is connected to a vacuum pump 20, preferably through a valve 30. Although the valve can be a simple block valve, it is preferred that the valve be an automatic valve which can control the pressure inside the sterilization chamber.

A tray 40 containing equipment to be sterilized is placed in the sterilization chamber, and the chamber is evacuated with the vacuum pump through the valve. A source of sterilant is placed in a vaporizer 50. The source of sterilant can be a liquid or a solid, but the sterilant has a vapor pressure less than the vapor pressure of water, and the vapor sterilant is condensable.

The source of sterilant in the vaporizer is preferably heated with a heater (not shown) to a temperature of approximately 60° C. to increase the vapor pressure of the sterilant. If the source of sterilant is a solid complex, higher temperatures than 60° C. may be required to release peroxide. If a solid complex is the source of sterilant, hydrogen peroxide can be evolved. The hydrogen peroxide will rapidly mix with water in the chamber to form vapor sterilant comprising hydrogen peroxide and water. Water can also be introduced with the sterilant into the chamber from the water in the environment or from the water in the complex. In the specification and in the claims, the term vapor sterilant will be understood to comprise sterilant and water. Also, the amount of water in the sterilant may vary, depending on the source of sterilant.

Sterilant and water vapor vaporize into the sterilization chamber. The vapor sterilant in the sterilization chamber sterilizes the exterior of the equipment in the chamber. The conditions in the chamber are chosen or are changed to conditions which cause condensation of the vapor sterilant on the equipment to be sterilized. The temperature of the equipment is approximately 20° C., and the temperature of the sterilization chamber is approximately 45° C. The vapor sterilant preferentially condenses on the equipment to be sterilized, because the equipment is cooler than the sterilization chamber. More detail on how the conditions are controlled to enhance condensing of the vapor sterilant will be given in the examples below. At least a portion of the vapor sterilant preferentially condenses in the interior of the lumens in the equipment to be sterilized.

The pressure of the sterilization chamber is then reduced with the vacuum pump to revaporize the condensed vapor. When the condensed vapor in the interior of the lumen vaporizes, it sterilizes the interior of the lumen. Further, when the pressure in the chamber is reduced to vaporize the condensed vapor, the water vaporizes preferentially before the sterilant and is removed by the vacuum pump, because the sterilant has a lower vapor pressure than water. Therefore, more water is removed from the chamber than sterilant. Because the condensed vapor is more concentrated in sterilant, the vapor which is generated from the condensed vapor also has a higher concentration of sterilant, enhancing its sterilizing effectiveness. The vapor sterilant can also diffuse into the interior of the lumen from the outside and sterilize the interior. Tables of vapor and liquid composition for hydrogen peroxide are given below, and the effects discussed above will become clearer through the examples.

The equipment remains in the sterilization chamber while the pressure in the sterilization chamber is held constant, reduced further, or allowed to increase. The diffusion and sterilization effectiveness of the vapor sterilant in the vacuum chamber varies depending on how the conditions in the interior of the chamber vary during the maintaining step. Alternatively, or in combination, the sterilization chamber can be vented to the outside atmosphere. Each of these embodiments will be discussed together with the effects on the sterilization of the interior of the lumens in detail in the examples below.

In another embodiment, the sterilant in the vaporizer can be concentrated by vaporizing water from the vaporizer and removing it from the sterilization chamber by removal through the vacuum pump. The concentrated sterilant in the vaporizer can then be vaporized into the sterilization chamber and condensed onto the equipment. By concentrating the sterilant in the vaporizer, the vapor sterilant is also concentrated, enhancing its effectiveness at sterilizing the equipment in the chamber. The remainder of the method is as above, evacuating to revaporize the condensed vapor and maintaining the equipment in the chamber while it is sterilized.

The data in Tables 1 and 2 below show the mole fraction of hydrogen vapor over hydrogen peroxide/water solutions and the total vapor pressure of the mixtures. The data in the tables can be used to show how the hydrogen peroxide becomes more concentrated through preferential vaporization of the water. The data are taken from "Hydrogen Peroxide" by Walter C. Schumb, Charles N. Satterfield, and Ralph L. Wentworth, pages 226–227, published in 1955.

TABLE 1

VAPOR COMPOSITION (MOLE FRACTION PEROXIDE) OVER HYDROGEN PEROXIDE - WATER SOLUTIONS

| Temp (° C.) | Mole Fraction Hydrogen Peroxide in Liquid | | | | | | | | |
|---|---|---|---|---|---|---|---|---|---|
| | 0.1 | 0.2 | 0.3 | 0.4 | 0.5 | 0.6 | 0.7 | 0.8 | 0.9 |
| 0 | 0.002 | 0.006 | 0.015 | 0.031 | 0.060 | 0.112 | 0.202 | 0.352 | 0.600 |
| 10 | 0.003 | 0.008 | 0.018 | 0.037 | 0.070 | 0.128 | 0.224 | 0.381 | 0.626 |
| 20 | 0.003 | 0.009 | 0.020 | 0.041 | 0.077 | 0.138 | 0.238 | 0.397 | 0.640 |
| 25 | 0.003 | 0.010 | 0.022 | 0.044 | 0.081 | 0.144 | 0.247 | 0.407 | 0.648 |
| 30 | 0.003 | 0.010 | 0.023 | 0.046 | 0.085 | 0.151 | 0.255 | 0.417 | 0.656 |
| 40 | 0.004 | 0.012 | 0.026 | 0.052 | 0.094 | 0.163 | 0.272 | 0.435 | 0.671 |
| 50 | 0.005 | 0.014 | 0.030 | 0.057 | 0.103 | 0.175 | 0.287 | 0.452 | 0.684 |
| 60 | 0.005 | 0.015 | 0.033 | 0.063 | 0.111 | 0.187 | 0.302 | 0.468 | 0.696 |
| 70 | 0.006 | 0.017 | 0.036 | 0.068 | 0.120 | 0.199 | 0.316 | 0.482 | 0.707 |
| 80 | 0.007 | 0.019 | 0.040 | 0.074 | 0.128 | 0.210 | 0.329 | 0.495 | 0.716 |
| 90 | 0.007 | 0.021 | 0.043 | 0.080 | 0.136 | 0.221 | 0.342 | 0.508 | 0.725 |
| 100 | 0.008 | 0.023 | 0.047 | 0.085 | 0.144 | 0.231 | 0.354 | 0.519 | 0.733 |
| 110 | 0.009 | 0.025 | 0.051 | 0.091 | 0.152 | 0.241 | 0.365 | 0.530 | 0.740 |
| 120 | 0.010 | 0.027 | 0.054 | 0.097 | 0.160 | 0.251 | 0.376 | 0.540 | 0.747 |
| 130 | 0.011 | 0.029 | 0.058 | 0.102 | 0.168 | 0.260 | 0.386 | 0.549 | 0.753 |
| 140 | 0.012 | 0.031 | 0.061 | 0.108 | 0.175 | 0.269 | 0.396 | 0.558 | 0.758 |
| 150 | 0.013 | 0.033 | 0.065 | 0.113 | 0.182 | 0.278 | 0.405 | 0.566 | 0.763 |

TABLE 2

TOTAL VAPOR PRESSURE (mm. Hg) OF HYDROGEN PEROXIDE - WATER SOLUTIONS

| Temp (° C.) | Mole Fraction Hydrogen Peroxide in Liquid | | | | | | | | | |
|---|---|---|---|---|---|---|---|---|---|---|
| | 0 | 0.1 | 0.2 | 0.3 | 0.4 | 0.5 | 0.6 | 0.7 | 0.8 | 0.9 |
| 0 | 4.58 | 4.06 | 3.45 | 2.81 | 2.20 | 1.66 | 1.21 | 0.856 | 0.593 | 0.404 |
| 10 | 9.20 | 8.17 | 6.96 | 5.7 | 4.49 | 3.42 | 2.53 | 1.83 | 1.30 | 0.915 |
| 20 | 17.5 | 15.6 | 13.3 | 10.9 | 8.69 | 6.68 | 5.00 | 3.66 | 2.64 | 1.89 |
| 25 | 23.7 | 21.1 | 18.1 | 14.9 | 11.9 | 9.17 | 6.90 | 5.09 | 3.71 | 2.69 |
| 30 | 31.8 | 28.3 | 24.3 | 20.1 | 16.0 | 12.4 | 9.41 | 6.99 | 5.14 | 3.77 |
| 40 | 55.3 | 49.3 | 42.4 | 35.2 | 28.3 | 22.2 | 17.0 | 12.8 | 9.55 | 7.14 |
| 50 | 92.6 | 82.5 | 71.1 | 59.3 | 48.1 | 37.9 | 29.3 | 22.4 | 17.0 | 12.9 |
| 60 | 149 | 133 | 115 | 96.6 | 78.7 | 62.6 | 49.0 | 37.8 | 29.1 | 22.5 |
| 70 | 234 | 209 | 181 | 152 | 125 | 100 | 79.0 | 61.8 | 48.2 | 37.8 |
| 80 | 355 | 318 | 216 | 233 | 192 | 155 | 124 | 97.8 | 77.2 | 61.3 |
| 90 | 526 | 471 | 410 | 348 | 289 | 235 | 189 | 150 | 120 | 96.5 |
| 100 | 760 | 682 | 595 | 507 | 422 | 346 | 280 | 226 | 182 | 148 |
| 110 | 1074 | 965 | 845 | 722 | 605 | 499 | 407 | 331 | 269 | 221 |
| 120 | 1489 | 1339 | 1175 | 1008 | 848 | 704 | 578 | 474 | 389 | 322 |
| 130 | 2025 | 1824 | 1604 | 1381 | 1168 | 974 | 807 | 666 | 552 | 460 |
| 140 | 2709 | 2443 | 2153 | 1860 | 1580 | 1326 | 1105 | 919 | 767 | 645 |
| 150 | 3568 | 3222 | 2847 | 2467 | 2105 | 1776 | 1489 | 1247 | 1048 | 887 |

Normally, the hydrogen peroxide solution in the vaporizer is approximately 59 wt % hydrogen peroxide. The 59 wt % hydrogen peroxide corresponds to 43.24 mole % hydrogen peroxide. The temperature of the vaporizer during the vaporization of the hydrogen peroxide is approximately 60° C.

From Table 1, the vapor over the 43 mole % hydrogen peroxide solution at 60° C. is approximately 6.3 mole % hydrogen peroxide. The vapor therefore contains almost 7 times less hydrogen peroxide than the solution from which it is vaporized. Water therefore preferentially vaporizes from the hydrogen peroxide solution, concentrating the hydrogen peroxide solution remaining in the vaporizer.

Similarly, when the condensed vapor on the equipment is vaporized, the vapor contains a higher mole fraction of water than in the condensed vapor, and the remaining condensed vapor on the equipment becomes more concentrated in hydrogen peroxide. When the pressure is lowered to below the vapor pressure of the sterilant, the concentration of sterilant in the vapor phase is higher than before water was vaporized from the condensed vapor.

Table 2 shows the total vapor pressure in mm of mercury for a range of hydrogen peroxide/water mixtures. The equipment in the chamber is at approximately 20° C. When the hydrogen peroxide in the vaporizer vaporizes, it will condense on the equipment if the pressure in the chamber is higher than the vapor pressure of the liquid. From Table 2, the vapor pressure of the 43.24 mole % hydrogen peroxide is approximately 75 torr at 60° C., the temperature of the vaporizer, but only about 8 torr at 20° C., the approximate temperature of the equipment. If the pressure in the chamber is above about 8 torr, the vapor will therefore condense. The pressure in the chamber can be increased by vaporizing more sterilant, by closing off the vacuum pump, by venting air into the sterilization chamber, or other suitable means. The Examples below show data generated by each of these means of increasing the pressure.

The first example is the control experiment, in which three different amounts of hydrogen peroxide was vaporized from the vaporizer and was not revaporized. The example also compares the sterilization efficiency with three different amounts of hydrogen peroxide. The method of Example 1 was not effective at sterilizing the interior of the lumens.

EXAMPLE 1

Vaporization of Hydrogen Peroxide from the Vaporizer Without Revaporizing Condensed Vapor In Example 1, the following items were placed in a CSR-wrapped tray in a 173 L sterilization chamber:

Open Petri dish
2.48 mm id×50 cm Teflon lumen
2.48 mm id×75 cm Teflon lumen
2.48 mm id×100 cm Teflon lumen
40 pieces of medical devices The Petri dish contained a biological challenge consisting of $2.2 \times 10^6$ *Bacillus stearothermophilus* spores on a stainless steel coupon. A coupon was also placed in the center of each of the three lumens. The coupon in the Petri dish was used as a test of the effectiveness of the method at sterilizing the exterior of a device, and the coupons in the lumens were a test of the effectiveness of sterilizing the interior of the lumens.

Three experiments were performed in which 1, 2, and 3 g of 59 wt % hydrogen peroxide were introduced into the vaporizer after the chamber was evacuated to 0.4 torr and allowed to vaporize and diffuse into the chamber for 5 minutes. All of the peroxide and water were vaporized and retained in the chamber. The results are shown in Table 3.

TABLE 3

Sterilization Tests With Vaporization of Three
Different Amounts of Hydrogen Peroxide Sterility Results

| Amount of Peroxide Used | In Open Petri Dish | In 2.48 mm × 50 cm Teflon lumen | In 2.48 mm × 75 cm Teflon lumen | In 2.48 × 100 cm Teflon lumen |
| --- | --- | --- | --- | --- |
| 1 g 59% | − | − | + | + |
| 2 g 59% | − | − | + | + |
| 3 g 59% | − | − | + | + |

Simply vaporizing hydrogen peroxide was effective at sterilizing the coupon in the Petri dish and the interior of 2.48 mm×50 cm lumen with all three amounts of hydrogen peroxide. Vaporizing the hydrogen peroxide was not effective at sterilizing the interior of either the 2.48 mm id×75 cm or the 2.48 mm id×100 cm lumen even when 3 g of hydrogen peroxide were used. Based on the test results, more peroxide in the chamber does not enhance the sterilization of the longer lumens.

Vaporizing hydrogen peroxide would thus sterilize the exterior of the device and the interior of shorter lumens but not the interior of longer lumens. As far as can be determined with these data, the sterilization efficiency did not vary with the amount of hydrogen peroxide vaporized.

In the next example, the test of Example 1 with 3 g of hydrogen peroxide was repeated with the additional feature of allowing the hydrogen peroxide vapor to diffuse for a longer period of time.

EXAMPLE 2

Sterilization Tests with Hydrogen Peroxide Vapor with Different Diffusion Times

In Example 2, the test of Example 1 with 3 g of 59% hydrogen peroxide was repeated with the addition of 20 minutes exposure time to the hydrogen peroxide vapor. The results are given in Table 4.

TABLE

Effect of Diffusion Time on Sterilization Efficiency

Sterility Results with 5 Minutes
Vaporization and X minutes Diffusion

| Diffusion Time | In Open Petri Dish | In 2.48 mm × 50 cm lumen | In 2.48 mm × 75 cm lumen | In 2.48 × 100 cm lumen |
| --- | --- | --- | --- | --- |
| 0 Minute | − | − | + | + |
| 20 Minutes | − | − | + | + |

Thus, even allowing the hydrogen peroxide vapor to diffuse for 20 minutes after vaporizing was not effective at sterilizing the interior of the lumens longer than 50 cm.

In Example 3, the hydrogen peroxide vapor was allowed to diffuse through the vacuum chamber at different pressures after vaporization.

EXAMPLE 3

Sterilization Tests Comparing Effects of Diffusion at Different Pressures

In Example 3, the pressure in the sterilization chamber was reduced to 0.4 torr, a total of 3 g of 59 wt % hydrogen peroxide was placed in the vaporizer, and the hydrogen peroxide was vaporized and diffused into the sterilization chamber for 5 minutes. The hydrogen peroxide was then allowed to diffuse at various pressures for 20 minutes. The pressure in the sterilization chamber was at constant pressure by controlling the pressure with an automatic valve between the sterilization chamber and the vacuum pump. The results are shown in Table 5.

TABLE 5

Effect of Diffusion Pressure on Sterilization Efficiency

Sterility Results with 5 Minutes
Vaporization and 20 Minutes Diffusion

| Diffusion Pressure | In Open Petri Dish | In 2.48 mm × 50 cm lumen | In 2.48 mm × 75 cm lumen | In 2.48 mm × 100 cm lumen |
| --- | --- | --- | --- | --- |
| Without pumpdown, final pressure about 9.5 torr | − | − | + | + |
| Reducing and controlling at 7 torr | − | − | − | + |
| Reducing and controlling at 6 torr | − | − | − | − |
| Reducing and controlling at 5 torr | − | − | − | − |
| Reducing and controlling at 4 torr | − | − | − | − |
| Reducing and controlling at 3 torr | − | − | − | − |
| Reducing and controlling at 2 torr | − | − | − | + |
| Reducing and controlling at 1 torr | − | − | + | + |

The experiment on the first line of Table 5 is the control experiment, in which the hydrogen peroxide was vaporized into the chamber and allowed to diffuse with the valve between the sterilization chamber and the vacuum pump closed. The pressure in the sterilization chamber was 9.5 torr, which is higher than the vapor pressure of 43 mole % hydrogen peroxide/water solution at 20° C., the approximate temperature of the equipment in the sterilization chamber, as shown in Table 2. The vaporized hydrogen peroxide therefore condensed onto the equipment in the sterilization chamber under these conditions.

The sterilization results were the same as for those on the second line of Table 4, because it is the same experiment, diffusion of the hydrogen peroxide vapor in a closed system for 20 minutes. The coupon in the Petri dish simulating the outside of the device was sterilized, but only the interior of the shortest 50 cm long lumen was sterilized. The interior surfaces of the longer 75 and 100 cm long lumens were not sterilized. Simple diffusion of hydrogen peroxide vapor from the outside is not effective at sterilizing the interior of long, narrow lumens, because peroxide condenses in the lumen before it can diffuse to the center of the lumen.

In the experiments described on the following lines of Table 5, the 3 grams of 59 wt % hydrogen peroxide was vaporized for 5 minutes. The vapor would condense on the equipment in the chamber, because the pressure in the sterilization chamber would be above the vapor pressure of the hydrogen peroxide solution at 20° C., the approximate temperature of the equipment in the chamber. At least a portion of the vapor would condense in the interior of the lumens.

The pressure in the sterilization chamber was then reduced, and the condensed vapor was vaporized and allowed to diffuse at constant pressure for 20 minutes. The interior of the sterilization chamber was maintained at a constant pressure by the automatic valve between the sterilization chamber and the vacuum pump. The constant pressure in the sterilization chamber ranged from 7 torr to 1 torr.

When the hydrogen peroxide vapor was allowed to diffuse at 7 torr, the interior surfaces of both the 50 cm and 75 long lumens were sterilized. Revaporization and diffusion of the hydrogen peroxide vapor at 7 torr was therefore effective at sterilizing the interior of the 75 cm long lumen, while the control experiment with diffusion at 9.5 torr was not effective at sterilizing the interior of the 75 cm long lumen. Although we do not wish to be tied to a theory, it is believed that the effectiveness of revaporizing the hydrogen peroxide and allowing the vapor to diffuse at 7 torr is due to a combination of vaporizing the condensed vapor in the inside of the lumen and diffusing of the hydrogen peroxide vapor both inside the lumen and from the outside into the interior of the lumen. The interior of the 100 cm long lumen was not sterilized when diffusion took place at 7 torr, however.

In the examples on the following lines, the same procedure was followed, vaporizing 3 g of 59 wt % hydrogen peroxide for 5 minutes and diffusing at constant pressure for 20 minutes. The constant diffusion pressure ranged from 1 to 6 torr.

In the experiments where the pressure was controlled between 3 and 6 torr, the interior surfaces of all three lumens were sterilized. Revaporization of the condensed vapor and diffusion of the vapor at constant pressure between 3 and 6 torr was therefore more effective at sterilizing the interior of the 100 cm long lumen than diffusion at 7 torr.

Although we do not wish to be restricted to a theory, it is believed that the greater effectiveness at sterilizing the interior of the long 100 cm lumen at the lower pressures is due to a combination of revaporization of the condensed vapor in the interior of the lumen and improved diffusion of the hydrogen peroxide vapor at the lower pressures.

When the constant pressure in the sterilization chamber during the 20 minute diffusion period was reduced to 2 torr, the interior of the 100 cm long lumen was no longer sterilized.

When the constant pressure in the sterilization chamber during the 20 minute diffusion period was reduced even further to 1 torr, neither the interior of the 75 cm long nor the interior of the 100 cm long lumen was sterilized. Revaporization of the condensed vapor and diffusion at lower pressures was therefore less effective at sterilizing the interior of long lumens than diffusion at the higher pressures of the earlier experiments.

While we again do not wish to be tied to a theory, it is believed that at the lower diffusion pressures of 1 and 2 torr, enough hydrogen peroxide is removed through maintaining the constant pressure by removing vapor through the vacuum pump to reduce the sterilization efficiency.

It is difficult to place limits on the optimal pressure range for diffusion of the revaporized vapor. The upper end of the range is the vapor pressure of the condensed hydrogen peroxide solution, because if the pressure exceeds the vapor pressure, the vapor will condense.

The lower end of the optimal range is more difficult to determine, because it is likely to be dependent on both the sterilization chamber and the equipment which is to be sterilized. Based on the data in Table 5, however, it appears that diffusion at 1 torr removes enough hydrogen peroxide vapor from the chamber to reduce the sterilization effectiveness, at least with this particular equipment and sterilization chamber. Although diffusion at 2 torr did not sterilize the interior of the 100 cm lumen, it was effective at sterilizing the interior of the 75 cm lumen. The sterilization efficiency at 2 torr is therefore higher than the control experiment where the hydrogen peroxide was not revaporized, but the efficiency was not as high as at higher diffusion pressures.

Vaporization of 3 g of 59 wt % hydrogen peroxide and diffusion in a sealed system for 20 minutes was therefore found to not be effective at sterilizing the interior of long lumens. When the condensed vapor was revaporized and allowed to diffuse at a pressure below the vapor pressure of the sterilant, the efficiency of sterilizing the interior of the longer lumens was enhanced, and the interiors of all three lumens were sterilized. When the constant pressure at which diffusion took place was either 1 or 2 torr, the efficiency of sterilization of the longer lumens decreased, but the efficiency was still higher than in the control experiment, with no revaporization. Revaporization of the condensed hydrogen peroxide vapor is therefore an effective method of sterilizing the interior of lumens.

In the following example, the method of Example 3 was followed, except that the valve between the sterilization chamber and the vacuum pump was closed when the diffusion pressure was reached. In Example 3, a constant pressure was maintained during the entire time for the diffusion of the hydrogen peroxide. In Example 4, the diffusion took place in a closed system, and the pressure was allowed to rise.

EXAMPLE 4

Effect of Diffusing Hydrogen Peroxide in a Closed System

In this example, the procedure of Example 3 was carried out, but the valve between the sterilization chamber and the vacuum pump was closed after the desired pressure was reached. In Example 3, constant pressure was maintained throughout the 20 minutes of diffusion. In Example 4, the valve was closed after the desired pressure was reached, and the pressure in the sterilization chamber was allowed to rise without adjustment.

The Petri dish and three lumens were placed in a tray in a 173 L sterilization chamber, and the chamber was evacuated to 0.4 torr. A total of 3 g of 59 wt % hydrogen peroxide was vaporized in the vaporizer and diffused into the sterilization chamber over a period of 5 minutes, and the pressure in the sterilization chamber was reduced to the desired value, and the valve between the sterilization chamber and the vacuum pump was closed. The hydrogen peroxide was then allowed to diffuse in the sterilization chamber for 20 minutes. The results are shown in Table 6 below.

TABLE 6

| Diffusion of Revaporized Hydrogen Peroxide with a Closed Valve | | | | |
|---|---|---|---|---|
| | Sterility Results with 5 Minutes Vaporization and 20 Minutes Diffusion | | | |
| Diffusion Pressure | In Open Petri Dish | In 2.48 mm × 50 cm Lumen | In 2.48 mm × 75 cm lumen | In 2.48 mm × 100 cm lumen |
| Valve closed at 2 torr, final pressure about 2.8 torr | − | − | − | − |
| Valve closed at 1 torr, | − | − | − | + |

TABLE 6-continued

Diffusion of Revaporized Hydrogen Peroxide with a Closed Valve

Sterility Results with 5 Minutes
Vaporization and 20 Minutes Diffusion

| Diffusion Pressure | In Open Petri Dish | In 2.48 mm × 50 cm Lumen | In 2.48 mm × 75 cm lumen | In 2.48 mm × 100 cm lumen |
|---|---|---|---|---|
| final pressure about 1.7 torr | | | | |

In the first experiment in Table 6, the valve was closed after the pressure reached 2 torr. The pressure in the sterilization chamber rose thereafter to about 2.8 torr. The interiors of all three lumens were sterilized. This result may be compared with those of Table 5, where the pressure was maintained at 2 torr. The interior of the 100 cm long lumen was not sterilized with that treatment.

In the second experiment of Table 6, the pressure was lowered to 1 torr, the valve was closed, and the pressure in the sterilization chamber rose to about 1.7 torr. The interiors of the 50 and 75 cm long lumens were sterilized, but the interior of the 100 cm long lumen was not. In the corresponding experiment in Table 5, where the pressure was maintained at 1 torr, the interior of only the 50 cm long lumen was sterilized. Closing the valve after the desired pressure was reached and allowing the hydrogen peroxide vapor to diffuse in a closed system was therefore more effective at sterilizing the long lumen with a constant pressure.

The sterilization results in both experiments in Table 6 with a closed valve were both more effective than the corresponding experiments in Table 5 where a constant pressure was used. Although we do not wish to tie the results to a theory, it is believed that when the pressure is maintained at a constant level during the diffusion, more hydrogen peroxide is removed from the system, reducing the sterilization efficiency. Both experiments in Table 6 were more effective at sterilizing the interior of lumens than the control experiment of Example 1, where the hydrogen peroxide was vaporized, but the condensed vapor was not revaporized. Even the experiment in Table 6 at 1 torr was more effective at sterilizing the interior of lumens than the control. Revaporizing the condensed hydrogen peroxide vapor in a variety of manners is effective at sterilizing the interior of lumens.

In the next example, the sterilization chamber was vented to 1 atmosphere before the allowing the hydrogen peroxide to diffuse.

EXAMPLE 5

Effect of Venting to 1 Atmosphere

In Example 5, the Petri dish and three lumens were placed in a tray with 40 medical devices in the sterilization chamber, the chamber was evacuated to 0.4 torr, 3 g of 57% hydrogen peroxide were vaporized into the chamber over 5 minutes, and the chamber was vented to 1 atmosphere. The hydrogen peroxide was then allowed to diffuse for a total of 20 minutes, either at 1 atmosphere pressure or 4 torr. The results are shown in Table 7 below.

TABLE 7

Effects of Venting Sterilization Chamber After Vaporization

Sterility Results with 5 Minutes Vaporization,
Venting to 1 atm., and 20 Minutes of Diffusion

| Diffusion Pressure | In Open Petri Dish | In 2.48 mm × 50 cm Lumen | In 2.48 × 75 cm Lumen | In 2.48 × 100 cm Lumen |
|---|---|---|---|---|
| 0.5 Minutes Vent Plus 19.5 Minutes at 1 Atm. | − | − | + | + |
| 0.5 Minutes Vent Plus 19.5 Minutes Reducing and Controlling at 4 Torr | − | − | − | − |

In the first experiment in Table 7, the sterilization chamber was vented to atmosphere after the hydrogen peroxide was vaporized into the sterilization chamber, and the hydrogen peroxide vapor was allowed to diffuse at 1 atmosphere for 19.5 minutes. Only the Petri dish and the interior of the shortest lumen, the 50 cm long lumen were sterilized. The interior of the 75 and the 100 cm long lumens were not sterilized. The first experiment was the control experiment for the second experiment.

In the second experiment in Table 7, the sterilization chamber was vented to atmosphere for 0.5 minutes, then the pressure in the sterilization chamber was reduced to 4 torr and controlled at that pressure for a total of 19.5 minutes. The interiors of all of the lumens were sterilized. The venting followed by diffusing the hydrogen peroxide at 4 torr was an effective method for sterilizing the interior of long narrow lumens.

The efficiency of sterilizing by venting and controlling at 4 torr was similar to that when the revaporized hydrogen peroxide diffused in the sterilization chamber while the chamber was maintained at a constant pressure of 4 torr.

Although we do not wish to be tied to a theory, it is believed venting the sterilization chamber can carry the hydrogen peroxide into the interior of the lumen. There may therefore be advantages to venting the chamber after vaporizing the hydrogen peroxide followed by revaporization and diffusion at low pressure, such as 4 torr.

The following example shows that the hydrogen peroxide can be revaporized multiple times.

EXAMPLE 6

Sterilization of Lumens Through Revaporizing the Hydrogen Peroxide Multiple Times In the following experiment, the condensed hydrogen peroxide was revaporized multiple times. The following procedure was followed in the experiment. A tray containing the Petri dish and three lumens with inoculated blades was placed in a 173 L sterilization chamber, as in the other examples, and the chamber was evacuated to 0.4 torr.

The experiment with multiple revaporizations was conducted as follows:
1. 3 grams of 59% hydrogen peroxide were introduced into the vaporizer.
2. The hydrogen peroxide was vaporized and introduced into the sterilization chamber over a period of 5 minutes.
3. The pressure was reduced to 4 torr for 5 minutes to revaporize the hydrogen peroxide.

4. The sterilization chamber was vented to 1 atmosphere pressure for 0.5 minutes to condense the vapor again.
5. The pressure in the sterilization chamber was reduced to 4 torr and maintained at a constant pressure of 4 torr for 14.5 minutes.

The total cycle lasted 25 minutes. The results are compared with a control experiment in Table 8 below.

TABLE 8

Sterilization of Lumens with a Multiple Revaporization Process

| | Sterility Results | | | |
|---|---|---|---|---|
| Test Conditions | In Open Petri Dish | In 2.48 mm × 50 cm Lumen | In 2.48 mm × 75 cm Lumen | In 2.48 mm × 100 cm Lumen |
| 5 Minutes Vaporization plus 20 Minutes Diffusion at 1 atm. | − | − | + | + |
| Cycle with Two-Vaporization Process | − | − | − | − |

Revaporizing the condensed hydrogen peroxide vapor was effective in sterilizing the interior of all three lumens, as shown by the data in Table 8. Revaporizing the condensed hydrogen peroxide twice was far more effective at sterilizing the interior of the lumens than the control experiment of vaporizing the hydrogen peroxide into the sterilization chamber and allowing the vapor to diffuse at 1 atmosphere pressure for 20 minutes.

Conclusions

The examples above demonstrate that this revaporization process provides an effective method to sterilize devices with long, narrow lumens. The method has several advantages over conventional methods.

1. The process does not require the temperature of the device be below 10° C. to obtain good sterilization efficiency. The device can be sterilized at room temperature.
2. The process does not require any liquid pretreatment of the lumen. It relies on diffusion, condensation, and revaporization of the sterilant in the lumen.
3. The revaporized sterilant has a higher concentration than the original sterilant vapor, because more water than sterilant is removed from the chamber. This concentrating process can enhance the overall efficiency.
4. Vapor condenses in the lumen when it diffuses into the lumen. If a process relies on condensed vapor for sterilization, then only the areas that are covered with the condensed vapor are sterilized. For certain lumens, the condensed vapor cannot cover the entire interior of the lumen. This new invention uses vapor to achieve sterilization. Sterilization with vapor is more effective than sterilization with liquid, because vapor diffuses and penetrates better than liquid. Once the condensed vapor is revaporized, it can diffuse further into the lumen.
5. The process is not very sensitive to pressure. Wide ranges of pressure can be used to vaporize the condensed vapor. The pressure may be held constant, increased, or decreased while sterilizing the lumen device.
6. The revaporization process can be further enhanced by an additional revaporization step before the condensation step. The additional revaporization further concentrates the sterilant, increasing its effectiveness.

While embodiments and applications of this invention have been shown and described, it should be apparent to those skilled in the art that many more modifications are possible without departing from the scope of the invention. The invention is not meant to be restricted, except in the spirit of the appended claims.

What is claimed is:

1. A method for sterilizing a device with a vapor sterilant, comprising:
   providing a chamber having a device disposed therein;
   introducing sterilant into said chamber from a source of sterilant, thereby forming a vapor sterilant;
   condensing said vapor sterilant in said chamber, thereby forming a condensed vapor on less than the entire surface of said device, said device being at a temperature below the condensation temperature of said vapor sterilant;
   revaporizing said condensed vapor to form a revaporized sterilant; and
   maintaining said device in the presence of said revaporized sterilant until said device is sterilized.

2. The method of claim 1, wherein said sterilant comprises hydrogen peroxide.

3. The method of claim 1, wherein said device comprises a diffusion-restricted area.

4. The method of claim 3, wherein said diffusion-restricted area is the interior of a lumen.

5. The method of claim 4, wherein said condensing of said vapor sterilant comprises condensing said vapor sterilant in the interior of said lumen, thereby forming a condensed vapor on less than the entire interior surface of said lumen.

6. The method of claim 5, wherein said revaporizing comprises revaporizing said condensed vapor in the interior of said lumen.

7. A method for sterilizing a device with a vapor sterilant, comprising:
   providing a chamber having a device disposed therein, wherein said device comprises a diffusion-restricted area;
   introducing sterilant into said chamber from a source of sterilant, thereby forming a vapor sterilant;
   condensing said vapor sterilant in said chamber, thereby forming a condensed vapor on less than the entire surface of said device;
   revaporizing said condensed vapor to form a revaporized sterilant; and
   maintaining said device in the presence of said revaporized sterilant until said device is sterilized.

8. The method of claim 7, wherein said diffusion-restricted area is the interior of a lumen.

9. The method of claim 8, wherein said condensing of said vapor sterilant comprises condensing said vapor sterilant in the interior of said lumen, thereby forming a condensed vapor on less than the entire interior surface of said lumen.

10. The method of claim 9, wherein said revaporizing comprises revaporizing said condensed vapor in the interior of said lumen.

11. The method of claim 1, wherein said revaporizing is accomplished by reducing the pressure in said chamber to below the vapor pressure of said vapor sterilant.

12. The method of claim 1, wherein said source of sterilant is a liquid, aqueous solution, or a solid.

13. The method of claim 1, wherein said source of sterilant is located in said chamber.

14. The method of claim 1, wherein said introducing comprises concentrating said source of sterilant.

15. The method of claim 1, wherein said condensing comprises increasing the pressure in said chamber to above the vapor pressure of said vapor sterilant.

16. The method of claim 1, wherein said condensing comprises venting said chamber to atmospheric pressure.

17. The method of claim 1, wherein said condensing comprises introducing more sterilant into said chamber.

18. The method of claim 1, wherein the pressure in said chamber is controlled by opening or closing a valve between said chamber and a vacuum pump.

19. The method of claim 1, wherein one or more steps are repeated one or more times in any order.

20. The method of claim 1, wherein said revaporizing said condensed vapor in said chamber comprises concentrating said vapor sterilant.

21. The method of claim 1, wherein said maintaining comprises maintaining said chamber at constant pressure.

22. The method of claim 1, wherein said maintaining comprises varying the pressure in said chamber.

23. The method of claim 1, additionally comprising exposing said device to plasma.

24. The method of claim 1, wherein said sterilant has a vapor pressure less than the vapor pressure of water.

25. A method for sterilizing a lumen device with a vapor sterilant, comprising:
   providing a chamber having a lumen device disposed therein, wherein said lumen device is more diffusion restricted than a Teflon reference lumen having an internal diameter of 2.48 mm and a length of 750 mm;
   introducing sterilant into said chamber from a source of sterilant, thereby forming a vapor sterilant;
   condensing said vapor sterilant in said chamber, thereby forming a condensed vapor;
   revaporizing said condensed vapor to form a revaporized sterilant; and
   maintaining said lumen device in the presence of said revaporized sterilant until said lumen device is sterilized, wherein there is no vessel containing a liquid attached to the lumen device during the maintaining stage.

26. The method of claim 25, wherein said sterilant comprises hydrogen peroxide.

27. The method of claim 25, wherein said revaporizing is accomplished by reducing the pressure in said chamber to below the vapor pressure of said vapor sterilant.

28. The method of claim 25, wherein said revaporizing said condensed vapor in said chamber comprises concentrating said vapor sterilant.

29. The method of claim 25, wherein said revaporizing comprises revaporizing said condensed vapor in the interior of said lumen.

* * * * *